United States Patent [19]
Kadin

[11] Patent Number: 4,791,131
[45] Date of Patent: Dec. 13, 1988

[54] ANALGESIC AND ANTIINFLAMMATORY 1-ACYL-2-OXINDOLE-3-CARBOXAMIDES

[75] Inventor: Saul B. Kadin, New London, Conn.

[73] Assignee: Pfizer Inc., New York, N.Y.

[21] Appl. No.: 140,056

[22] Filed: Dec. 31, 1987

Related U.S. Application Data

[60] Division of Ser. No. 14,120, Feb. 2, 1987, Pat. No. 4,730,004, which is a continuation-in-part of Ser. No. 821,296, Jan. 22, 1986, abandoned, which is a continuation-in-part of Ser. No. 753,200, Jul. 9, 1985, abandoned.

[51] Int. Cl.$^4$ .................... A61K 31/40; A61K 31/44; C07D 209/34
[52] U.S. Cl. .................... 514/418; 514/339; 514/371; 514/372; 514/378; 514/380; 514/397; 514/414; 546/273; 548/181; 548/214; 548/233; 548/245; 548/246; 548/336; 548/467; 548/486
[58] Field of Search ............... 514/418, 339, 371, 372, 514/378, 380, 397, 414; 548/486, 181, 214, 233, 245, 246, 336, 467; 546/273

[56] References Cited

U.S. PATENT DOCUMENTS

| | | | |
|---|---|---|---|
| 3,190,889 | 6/1965 | Shen | 260/319 |
| 3,632,587 | 1/1972 | Hollowood | 548/486 X |
| 3,634,453 | 1/1972 | McManus et al. | 260/325 |
| 4,569,942 | 2/1986 | Kadin | 514/414 |
| 4,730,004 | 3/1988 | Kadin | 514/418 |

OTHER PUBLICATIONS

Tacconi, et al., Tetrahedron, 27, (1971) pp. 561–579.
C.A., 51: 5044a (1957), Kisteneva.

*Primary Examiner*—Joseph Paul Brust
*Attorney, Agent, or Firm*—Peter C. Richardson; J. Trevor Lumb

[57] ABSTRACT

Certain new 2-oxindole-3-carboxamide compounds having an acyl substituent at the 1-position are inhibitors of the cyclooxygenase (CO) and lipoxygenase (LO) enzymes, and are useful as analgesic and anti-inflammatory agents in mammalian subjects. In particular, the compounds of the invention are useful for acute administration for ameliorating or eliminating pain in human subjects recovering from surgery or trauma, and also for chronic administration for alleviating the symptoms of chronic diseases, such as rheumatoid arthritis and osteoarthritis, in human subjects.

9 Claims, No Drawings

ANALGESIC AND ANTIINFLAMMATORY 1-ACYL-2-OXINDOLE-3-CARBOXAMIDES

CROSS-REFERENCE TO RELATED APPLICATIONS

This application is a division of application Ser. No. 07/014,120, filed Feb. 2, 1987, now U.S. Pat. No. 4,730,004 which is a continuation in part of application Ser. No. 06/821,296 filed Jan. 22, 1986, now abandoned, which is a continuation in part of application Ser. No. 06/753,200, filed July 9, 1985, now abandoned.

BACKGROUND OF THE INVENTION

This application relates to new chemical compounds which are of value as new medicinal agents. More particularly the new chemical compounds are derivatives of 2-oxindole-3-carboxamide, and they are further substituted at the 1-position by an acyl group. These new chemical compounds are inhibitors of both the cyclooxygenase (CO) and lipoxygenase (LO) enzymes.

The compounds of this invention are useful as analgesic agents in mammals, particularly man, and they are of use for acute administration for ameliorating or eliminating pain, such as the pain experienced by patients recovering from surgery or trauma.

In addition to their usefulness for acute administration to combat pain, the compounds of this invention are useful for chronic administration to mammals, particularly man, to alleviate the symptoms of chronic diseases, such as the inflammation and pain associated with rheumatoid arthritis and osteoarthritis.

SUMMARY OF THE INVENTION

This invention provides novel 1-acyl-2-oxindole-3-carboxamide compounds of the formula

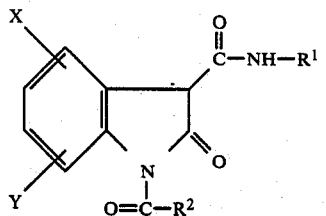

and the pharmaceutically-acceptable base salts thereof; wherein

X and Y are each selected from the group consisting of hydrogen, fluoro, chloro, bromo, trifluoromethyl and alkyl having 1 to 4 carbons;

$R^1$ is selected from the group consisting of alkyl having from 1 to 6 carbons, cycloalkyl having from 3 to 7 carbons, heterocyclic, mono-methyl heterocyclic, furylmethyl, thienylmethyl and groups of the formula

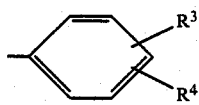

wherein said heterocyclic is selected from the group consisting of pyridyl, thienyl, furyl, pyrrolyl, thiazolyl, oxazolyl, imidazolyl, isothiazolyl and isoxazolyl;

and $R^3$ and $R^4$ are each selected from the group consisting of hydrogen, fluoro, chloro, alkyl having 1 to 4 carbons, alkoxy having 1 to 4 carbons and trifluoromethyl;

and $R^2$ is alkyl having 1 to 6 carbons.

Said compounds of formula I are active as analgesic agents and as agents for treating inflammatory diseases such as arthritides. Accordingly, this invention provides a method of eliciting an analgesic response in a mammalian subject, especially man; a method of treating an inflammatory disease in a mammalian subject, especially man; and pharmaceutical compositions comprising a compound of formula I and a pharmaceutically-acceptable carrier.

A preferred group of compounds of this invention consists of the compounds of the formula I, wherein X and Y are as defined previously, $R^1$ is said

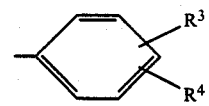

and $R^2$ is methyl. Within this preferred group, particularly preferred compounds are: (i) those wherein X and Y are both hydrogen; (ii) those wherein X is 5-chloro and Y is hydrogen; and (iii) those wherein X is 5-chloro and Y is 6-fluoro.

Especially preferred individual compounds of the invention are:

N-phenyl-1-acetyl-2-oxindole-3-carboxamide;
N-(4-fluorophenyl)-5-chloro-1-acetyl-2-oxindole-3-carboxamide;
N-(2,4-dichlorophenyl)-5-chloro-1-acetyl-2-oxindole-3-carboxamide;
N-phenyl-5-chloro-6-fluoro-1-acetyl-2-oxindole-3-carboxamide; and
N-(4-chlorophenyl)-5-chloro-6-fluoro-1-acetyl-2- oxindole-3-carboxamide.

DETAILED DESCRIPTION OF THE INVENTION

This invention relates to the compound of formula I, and these compounds are named as derivatives of 2-oxindole, the compound formula II:

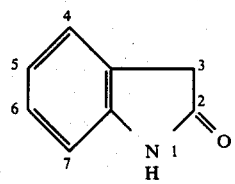

Additionally, as will be appreciated by one skilled in the art, the analgesic and antiinflammatory compounds of this invention of formula I, wherein X, Y, $R^1$ and $R^2$ are defined previously, are capable of enolization, and therefore they can exist in one or more tautomeric (enolic) forms. All such tautomeric (enolic) forms of the compounds of formula I are considered to be within the scope of this invention.

The compounds of the formula I are prepared from the appropriate 2-oxindole compound of the formula III:

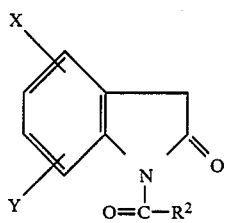
(III)

by attaching the substituent —C(=O)—NH—R¹ to the 3-position. This entails reacting a compound of the formula III with an isocyanate compound of the formula R¹—N=C=O. The reaction is usually carried out by contacting the 2-oxindole of formula III with from 1.0 to 1.5, preferably about 1.1, molar equivalents of the isocyanate of formula R¹—N=C=O in a reaction-inert, organic solvent, in the presence of from one to four molar equivalents of a base. A reaction-inert solvent is one which will dissolve at least one of the reactants and does not adversely interact with any of the reactants or the products. However, in practice, a polar, aprotic solvent, such as N,N-dimethylformamide, N,N-dimethylacetamide, N-methylpyrrolidone or dimethyl sulfoxide is commonly used. A variety of basic agents can be used, but preferred agents are tertiary organic amines, especially triethylamine, tributylamine, N-methylmorpholine, N-methylpiperidine and 4-(N,N-dimethylamino)pyridine.

The 2-oxindole of the formula III, the isocyanate of the formula R¹—N=C=O and the basic agent are normally combined initially in the cold, e.g., at a temperature from -10° to 5° C. The reaction mixture is then usually stirred at about 0° C. for a few hours and then at room temperature until the reaction is complete. Conveniently, the progress of the reaction is monitored by thin-layer chromatography. At this point, the reaction mixture is normally poured into an excess of water and resulting mixture is acidified to a pH from 1 to 5 using a mineral acid, e.g., hydrochloric acid, or the reaction mixture is poured directly into an excess of dilute hydrochloric acid. If the product is out of solution as a solid at this point, it can be recovered by filtration; alternatively it can be recovered by the normal procedure of solvent extraction. The crude product thus obtained can be purified by conventional procedures, such recrystallization from an appropriate solvent system or by chromatography.

The 2-oxindole starting materials of the formula III can be prepared by reaction of a 2-oxindole of the formula

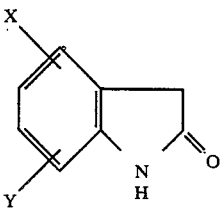
(IV)

with the appropriate acid anhydride of the formula (R²—CO)₂O. Usually the compound of formula IV is reacted with from one to three equivalents, and preferably 1.2 to 1.5 equivalents, of the anhydride in the absence of solvent, at a temperature in the range from 80° to 130° C., and preferably about 100° C., for several hours (e.g., about 4 hours). If desired, however, an inert solvent such as toluene can be added. At the end of the reaction, the product of formula III can be recovered by removal of the excess anhydride and any solvent by evaporation. The crude product can be used for conversion into a compound of formula I, or, preferably, the crude product can be purified by standard methods such as recrystallization or chromatography.

The 2-oxindole compounds of formula IV are prepared by known methods, or methods analogous to known methods. Consult: "Rodd's Chemistry of Carbon Compounds," Second Edition, S. Coffey editor, Volume IV Part A, Elsevier Scientific Publishing Company, 1973, pp. 448-450; Gassman et al.,*Journal of Organic Chemistry*, 42, 1340 (1977); Wright et al., *Journal of the American Chemical Society*, 78, 221 (1956); Beckett et al., *Tetrahedron*, 24, 6093 (1968); U.S. Pat. Nos. 3,882,236, 4,006,161 and 4,160,032; Walker, *Journal of the American Chemical Society*, 77, 3844 (1955); Protiva et al., *Collection of Czechoslovakian Chemical Communications*, 44, 2108 (1979); McEvoy et al., *Journal of Organic Chemistry*, 38, 3350 (1973); Simet, *Journal of Organic Chemistry*, 28, 3580 (1963); Wieland et al., *Chemische Berichte*, 96, 253 (1963); and references cited therein.

The compounds of the formula I are acidic and they form base salts. All such base salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate. Typical salts of the compounds of formula I which can be prepared are primary, secondary and tertiary amine salts, alkali metal salts and alkaline earth metal salts. Especially valuable are the ethanolamine, diethanolamine, triethanolamine, sodium and potassium salts.

Basic agents suitably employed in salt formation belong to both the organic and inorganic types, and they include organic amines, alkali metal hydroxides, alkali metal carbonates, alkali metal bicarbonates, alkali metal hydrides, alkali metal alkoxides, alkaline earth metal hydroxides, alkaline earth metal carbonates, alkaline earth metal hydrides and alkaline earth metal alkoxides. Representative examples of such bases are primary amines, such as n-propylamine, n-butylamine, aniline, cyclohexylamine, benzylamine, p-toluidine, ethanolamine and glucamine; secondary amines, such as diethylamine, diethanolamine, N-methylglucamine, N-methylaniline, morpholine, pyrrolidine and piperidine; tertiary amines, such as triethylamine, triethanolamine, N,N-dimethylaniline, N-ethylpiperidine and N-methylmorpholine; hydroxides, such as sodium hydroxide; alkoxides, such as sodium ethoxide and potassium methoxide; hydrides, such as calcium hydride and sodium hydride; and carbonates, such as potassium carbonate and sodium carbonate.

The compounds of formula I possess analgesic activity. This activity has been demonstrated in mice by showing blockade of the abdominal stretching induced by administration of 2-phenyl-1,4-benzoquinone (PBQ), using a method based on that of Siegmund et al., *Proc. Soc. Exp. Biol. Med.*, 95, 729–731, (1957), as adapted for high throughput (see further Milne and Twomey,

*Agents and Actions,* 10, 31–37, [1980]). The mice used in these experiments were Carworth males, albino CF-1 strain, weighing 18–20 g. All mice were fasted overnight prior to drug administration and testing.

The compounds of formula I were dissolved or suspended in a vehicle consisting of ethanol (5%), emulphor 620 (a mixture of polyoxyethylene fatty acid ester, 5%) and saline (90%). This vehicle also served as control. Doses were on a logarithmic scale (i.e., . . . 0.32, 1.0, 3.2, 10, 32 . . . mg/kg). The route of administration was oral, with concentrations varied to allow a constant dosage volume of 10 ml/kg of body weight. The aforesaid method of Milne and Twomey was used to determine efficacy and potency. Mice were treated with compounds orally, and one hour later received PBQ, 2 mg/kg, intraperitoneally. Individual mice were then immediately placed in a warmed, Lucite (transparent plastic) chamber, and, starting five minutes after PBQ administration, the number of abdominal constrictions during the subsequent 5 minutes was recorded. The degree of analgesic protection (% MPE) was calculated on the basis of suppression of abdominal constriction relative to counts from response data for generation of an $MPE_{50}$, the best estimate of the dose that reduces abdominal constriction to 50% of control levels.

The compounds of formula I also possess antiinflammatory activity. This activity has been demonstrated in rats by a method based on the standard carrageenin-induced rat-foot edema test. (Winter et al., *Proc. Soc. Exp. Biol. Med.,* 111, 544 [1963]).

Unanesthetized, adult, male, albino rats of 150 g to 190 g body weight were numbered, weighed, and an ink mark placed on the right lateral malleolus. Each paw was immersed in mercury exactly to the ink mark. The mercury was contained in a glass cylinder, connected to a Statham Pressure Transducer. The output from the transducer was fed through a control unit to a microvoltameter. The volume of mercury displaced by the immersed paw was read. Drugs were given by gavage. One hour after drug administration, edema was induced by injection of 0.05 ml of 1% solution of carrageenin into the plantar tissue of the marked paws. Immediately thereafter, the volume of the injected foot was measured. The increase in foot volume 3 hours after the injection of carrageenin constitutes the individual inflammatory response.

The analgesic activity of the compounds of formula I makes them useful for acute administration to mammals for the control of pain, e.g., post-operative pain and the pain of trauma. Additionally the compounds of formula I are useful for chronic administration to mammals for the alleviation of the symptoms of chronic diseases, such as the inflammation of rheumatoid arthritis, and the pain associated with osteoarthritis and other musculoskeletal disorders.

When a compound of the formula I or a pharmaceutically acceptable salt thereof is to be used as either an analgesic agent or an anti-inflammatory agent, it can be administered to a mammalian subject either alone, or, preferably, in combination with pharmaceutically-acceptable carriers or diluents in a pharmaceutical composition, according to standard pharmaceutical practice. A compound can be administered orally or parenterally. Parenteral administration includes intravenous, intramuscular, intraperitoneal, subcutaneous and topical administration.

In a pharmaceutical composition containing a compound of formula I, or a pharmaceutically-acceptable salt thereof, the weight ratio of carrier to active ingredient will normally be in the range from 1:4 to 4:1, and preferably 1:2 to 2:1. However, in any given case, the ratio chosen will depend on such factors as the solubility of the active component, the dosage contemplated and the precise route of administration.

For oral use of a compound of formula I of this invention, the compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled to render the preparation isotonic.

When a compound of formula I or salt thereof is used in a human subject, the daily dosage will normally be determined by the prescribing physician. Moreover, the dosage will vary according to the age, weight and response of the individual patient, as well as the severity of the patient's symptoms and the potency of the particular compound being administered. However, for acute administration to relieve pain, an effective analgesic response eliciting dose in most instances will be 0.1 to 1.0 g as needed (e.g., every four to six hours). For chronic administration to alleviate (treat) inflammation and pain, in most instances an effective dose will be from 0.1 to 1.5 g per day, and preferably 0.3 to 1.0 g per day, in single or divided doses. On the other hand, it may be necessary to use dosages outside these limits in some cases.

The following examples and preparations are being provided solely for the purpose of further illustration.

EXAMPLE 1

N-Phenyl-1-acetyl-2-oxindole-3-carboxamide

A solution prepared from 0.7 g (4.03 mmole) of 1-acetyl-2-oxindole, 1.02 g (8.34 mmole) of 4-(N,N-dimethylamino)pyridine and 10 ml of N,N-dimethylformamide was cooled in 0° C. under nitrogen, and then a solution of 0.48 ml (4.4 mmole) of phenyl isocyanate in 5 ml of N,N-dimethylformamide was added dropwise with stirring. Stirring was continued at 0° C. for several hours, and then at room temperature until analysis by thin layer chromatography indicated complete reaction of the 1-acetyl-2-oxindole. The reaction mixture was poured onto 500 ml 2N hydrochloric acid containing crushed ice, and the solid which formed was recovered by filtration. This afforded 900 mg of crude title product.

The crude product was triturated under diethyl ether, and then it was recrystallized from a mixture of dichloromethane and isopropanol. This afforded 300 mg of the title compound as white crystals, m.p. 207°–209° C.

The infrared spectrum (KBr disk) showed absorptions at 3440, 1765, 1725 and 1660 $cm^1$.

The $^1H$ nuclear magnetic resonance spectrum ($CDCl_3$) showed absorptions at 2.75 (s, 3H), 4.6 (s, 1H), 7.1–7.5 (m, 5H), 7.6 (d, 2H, J=8.5 Hz), 7.8 (d, 1H, J=8.5 Hz), 8.25 (d, 1H, J=8.5 Hz) and 8.85 (bs, 1H) ppm downfield from internal tetramethylsilane.

Analysis: Calculated for $C_{17}H_{14}N_2O_3$: C, 69.38; H, 4.79; N, 9.52%. Found: C, 68.99; H, 4.78; N, 9.44%.

Reaction of 1-acetyl-2-oxindole with 2-furylmethyl isocyanate and with 2-thienylemthyl isocyanate, using the above procedure, affords N-(2-furylmethyl)-1-acetyl-2-oxindole-3-carboxamide and N-(2-thienylmethyl)-1-acetyl-2-oxindole-3-carboxamide, respectively.

EXAMPLE 2

Reaction of the appropriate 1-acyl-2-oxindole with the requisite isocyanate, according to the procedure of Example 1, afforded the compounds in Table I. In some cases the crude product was recrystallized from toluene, since the use of isopropanol sometimes leads to ester formation at the 3-position.

TABLE I

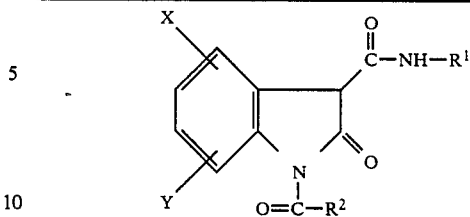

| X | Y | $R^1$ | $R^2$ | Melting Point (°C.) |
|---|---|---|---|---|
| H | H | 2,4-difluorophenyl | methyl | 200–202 |
| H | H | 3-trifluoromethylphenyl | methyl | 181–182.5 |
| H | H | 2,4-dichlorophenyl | methyl | 207–209 |
| H | H | 4-chlorophenyl | methyl | 218–220 |
| H | H | 4-methoxyphenyl | methyl | 220–225 |
| 5-Cl | H | phenyl | methyl | 203–205 |
| 5-Cl | H | 4-fluorophenyl | methyl | 220–225 |
| 5-Cl | H | 2,4-difluorophenyl | methyl | 208–210 |
| 5-Cl | H | 2,4-dichlorophenyl | methyl | 207–209 |
| 5-Cl | H | 4-chlorophenyl | methyl | 226–227 |
| 5-Cl | H | 3-trifluoromethylphenyl | methyl | 213–215 |
| 5-Cl | H | 4-methoxyphenyl | methyl | 219–221 |
| 5-F | 6-Cl | phenyl | methyl | 220–221 |
| 5-Cl | H | phenyl | isopropyl | 200–201 |
| 5-Cl | H | 2,4-dichlorophenyl | isopropyl | 211–213 |
| 5-Cl | H | 2,4-difluorophenyl | isopropyl | 174–177 |
| 5-Cl | H | 4-chlorophenyl | isopropyl | 212–213 |
| 6-F | H | phenyl | methyl | 204–205 |
| 6-F | H | 4-chlorophenyl | methyl | 211.5–213.5 |
| 5-Cl | H | 4-tolyl | methyl | 238–240 |
| 5-Cl | H | 2-pyridyl | methyl | 250–253 |
| 5-Cl | H | 2,4-dimethylphenyl | methyl | 215–217 |
| 5-F | H | 4-chlorophenyl | methyl | 201–203 |
| 6-F | H | 2,4-dichlorophenyl | methyl | 193–194 |
| 5-F | H | phenyl | methyl | 210–213 |
| 5-F | H | 2,4-dichlorophenyl | methyl | 222–225 |
| 5-F | 6-F | phenyl | methyl | 212–213 |
| 5-F | 6-F | 4-chlorophenyl | methyl | 225–226 |
| 5-F | 6-F | 4-tolyl | methyl | 204–206 |
| 5-Cl | 6-F | phenyl | methyl | 206–207 |
| 5-Cl | 6-F | 4-chlorophenyl | methyl | 258–259 |
| 5-Cl | 6-F | 4-tolyl | methyl | 215–218 |
| 5-6 | H | 2,6-dichlorophenyl | methyl | 228–231 |

EXAMPLE 3

The compounds in Table II, below, can be prepared by reaction of the appropriate 1-acyl-2-oxindole with the requisite isocyanate, using the procedure of Example 1.

TABLE II

| X | Y | $R^1$ | $R^2$ |
|---|---|---|---|
| 5-$CF_3$ | H | 3-tolyl | methyl |
| 5-F | H | cyclopropyl | ethyl |
| 6-Cl | H | 3-isobutoxyphenyl | ethyl |
| 7-F | H | 4-n-butylphenyl | methyl |
| 6-$CF_3$ | H | 3,4-dimethoxyphenyl | methyl |
| 4-Cl | H | 3-chloro-4-fluorophenyl | methyl |
| 6-Br | H | cycloheptyl | methyl |
| 5-Cl | 6-Cl | 3,4-dichlorophenyl | n-hexyl |
| 5-F | 6-F | n-hexyl | methyl |
| 5-n-$C_4H_9$ | H | cyclohexyl | methyl |
| 5-$CH_3$ | 6-F | methyl | methyl |
| 4-$CH_3$ | 5-$CH_3$ | 3-pyridyl | methyl |
| H | H | 6-methyl-2-pyridyl | methyl |
| 5-Cl | 6-Cl | 2-thienyl | ethyl |
| H | H | 3-thienyl | isopropyl |
| 6-Cl | H | 2-thiazolyl | methyl |
| 5-$CF_3$ | H | 5-methyl-2-thiazolyl | ethyl |
| 5-$CH_3$ | 6-$CH_3$ | 2-furyl | n-hexyl |
| 5-F | H | 2-oxazolyl | methyl |
| H | H | 2-pyrrolyl | ethyl |
| H | H | 4-pyridyl | methyl |
| H | H | 2-imidazolyl | methyl |
| 5-Cl | H | 5-isothiazolyl | methyl |
| 5-F | 6-F | 5-methyl-3-isoxazolyl | methyl |

PREPARATION 1

5-Chloro-2-oxindole

To a stirred slurry of 100 g (0.55 mol) of 5-chloroisatin in 930 ml of ethanol was added 40 ml (0.826 mol) of hydrazine hydrate, resulting in a red solution. The solution was heated under reflux for 3.5 hours, during which time a precipitate appeared. The reaction mixture was stirred overnight, and then the precipitate was recovered by filtration to give 5-chloro-3-hydrazono-2-oxindole as a yellow solid, which was dried in a vacuum oven. The dried solid weighed 105.4 g.

The dried solid was then added portionwise, during 10 minutes, to a solution of 125.1 g of sodium methoxide in 900 ml of absolute ethanol. The resultant solution was heated under reflux for 10 minutes and then it was concentrated in vacuo to a gummy solid. The gummy solid was dissolved in 400 ml of water and the aqueous solution thus obtained was decolorized with activated carbon and then poured into a mixture of 1 liter of water and 180 ml of concentrated hydrochloric acid containing ice chips. A tan solid precipitated and it was collected by filtration and washed thoroughly with water. The solid was dried and then it was washed with diethyl ether. Finally it was recrystallized from ethanol to give 48.9 g of the title compound, m.p. 193°–195° C. (dec).

In an analogous fashion, 5-methylisatin was converted into 5-methyl-2-oxindole by treatment with hydrazine hydrate followed sodium ethoxide in ethanol. The product melted at 173°–174° C.

PREPARATION 2

4,5-Dimethyl-2-oxindole and 5,6-Dimethyl-2-oxindole 3,4-Dimethylaniline was converted into 3,4-dimethylisonitrosoacetanilide by reaction with chloral hydrate and hydroxylamine, using the method described in "Organic Syntheses," Collective Volume I, page 327. The 3,4-dimethyl-isonitrosoacetanilide was cyclized with sulfuric acid, according to the method of Baker et al., *Journal of Organic Chemistry*, 17, 149 (1952), to give 4,5-dimethylisatin (m.p. 225°–226° C.) and 5,6-dimethylisatin (m.p. 217°–218° C.).

4,5-Dimethylisatin was converted into 4,5-di-methyl-2-oxindole, m.p. 245.5°–247.5° C., by treatment with hydrazine hydrate, followed by sodium ethoxide in ethanol, substantially according to the procedure of Preparation 1.

In like manner, 5,6-dimethylisatin was converted into 5,6-dimethyl-2-oxindole, m.p. 196.5°–198° C., by treatment with hydrazine hydrate, followed by sodium ethoxide in ethanol, substantially according to the procedure of Preparation 1.

PREPARATION 3

4-Chloro-2-oxindole and 6-Chloro-2-oxindole

A. 3-Chloro-isonitrosoacetanilide

To a stirred solution of 113.23 g (0.686 mol) of chloral hydrate in 2 liters of water was added 419 g (2.95 mol) of sodium sulfate, followed by a solution prepared from 89.25 g (0.70 mol) of 3-chloroaniline, 62 ml of concentrated hydrochloric acid and 500 ml of water. A thick precipitate formed. To the reaction mixture was then added, with stirring, a solution of 155 g (2.23 mol) of hydroxylamine in 500 ml of water. Stirring was continued and the reaction mixture was warmed slowly and it was maintained between 60° and 75° C. for approximately 6 hours, during which time an additional 1 liter of water as added to facilitate stirring. The reaction mixture was then cooled and the precipitate was recovered by filtration. The wet solid was dried to give 136.1 g of 3-chloro-isonitrosoacetanilide.

B. 4-Chloroisatin and 6-chloroisatin

To 775 ml of concentrated sulfuric acid, preheated to 70° C., was added, with stirring, 136 g of 3-chloroisonitrosoacetanilide at such a rate as to maintain the reaction medium at a temperature between 75° and 85° C. When all the solid had been added, the reaction mixture was heated at 90° C. for an additional 30 minutes. The reaction mixture was then cooled, and poured slowly onto ca. 2 liters of ice, with stirring. Additional ice was added as necessary to maintain the temperature below room temperature. A red-orange precipitate formed which was recovered by filtration, washed with water and dried. The resultant solid was slurried in 2 liters of water, and then it was brought into solution by the addition of ca. 700 ml of 3N sodium hydroxide. The solution was filtered, and then pH was adjusted to 8 with concentrated hydrochloric acid. At this point, 120 ml of a mixture of 80 parts water and 20 parts concentrated hydrochloric acid was added. The solid which precipitated was recovered by filtration, washed with water and dried to give 50 g of crude 4-chloroisatin. The filtrate from which the 4-chloroisatin had been recovered was further acidified to pH 0 using concentrated hydrochloric acid, whereupon a further precipitate formed. It was recovered by filtration, washed with water and dried, to give 43 g of crude 6-chloroisatin.

The crude 4-chloroisatin was recrystallized from acetic acid to give 43.3 g of material melting at 258°–259° C.

The crude 6-chloroisatin was recrystallized from acetic acid to give 36.2 g of material melting at 261°–262° C.

C. 4-Chloro-2-oxindole

To a stirred slurry of 43.3 g of 4-chloroisatin in 350 ml of ethanol was added 17.3 ml of hydrazine hydrate, and then the reaction mixture was cooled, and the precipitate was recovered by filtration to give 43.5 g of 4-chloro-3-hydrazono-2-oxindole, m.p. 235°–236° C.

To a stirred solution of 22 g of sodium in 450 ml of anhydrous ethanol was added, portionwise, 43.5 g of 4-chloro-3-hydrazono-2-oxindole, and the resulting solution was heated under reflux for 30 minutes.

The cooled solution was then concentrated to a gum, which was dissolved in 400 ml of water and decolorized using activated carbon. The resulting solution was poured onto a mixture of 1 liter of water and 45 ml of concentrated hydrochloric acid. The precipitate which formed was recovered by filtration, dried and recrystallized from ethanol, giving 22.4 g of 4-chloro-2-oxindole, m.p. 216°–218° C. (dec).

D. 6-Chloro-2-oxindole

Reaction of 36.2 g of 6-chloroisatin with hydrazine hydrate followed by sodium ethoxide in ethanol, substantially according to C above, afforded 14.2 g of 6-chloro-2-oxindole, m.p. 196°–198° C.

PREPARATION 4

5,6-Difluoro-2-oxindole

Reaction of 3,4-difluoroaniline with chloral hydrate and hydroxylamine followed cyclization with sulfuric acid, in a manner analogous to Parts A and B of Preparation 3, gave 5,6-difluoroisatin, which was reacted with hydrazine hydrate followed by sodium methoxide in ethanol, in a manner analogous to Preparation 1, to give the title compound, m.p. 187°–190° C.

PREPARATION 5

5-Fluoro-2-oxindole

To a stirred solution of 11.1 g (0.1 mol) of 4-fluoroaniline in 200 ml of dichloromethane, at −60° to −65° C., was added, dropwise, a solution of 10.8 g (0.1 mol) of t-butyl hypochlorite in 25 ml of dichloromethane. Stirring was continued for 10 minutes at −60° to −65°, and then was added, dropwise, a solution of 13.4 g (0.1 mol) of ethyl 2-(methylthio)acetate in 25 ml of dichloromethane. Stirring was continued at −60° C. for 1 hour and then was added, dropwise, at −60° to −65° C., a solution of 11.1 g (0.11 mol) of triethylamine in 25 mol of dichloromethane. The cooling bath was removed, and when the reaction mixture had warmed to room temperature, 100 ml of water was added. The phases were separated, and the organic phase was wahed with saturated sodium chloride solution, dried ($Na_2SO_4$) and evaporated in vacuo. The residue was dissolved in 350 ml of diethyl ether, to which was added 40 ml of 2N hydrochloric acid. This mixture was stirred at room temperature overnight. The phases were separated and the ether phase was washed with water, followed saturated sodium chloride. The dried ($Na_2SO_4$) ether phase was evaporated in vacuo to give 17 g of an orange-brown solid which was triturated under isopropyl ether. The solid was then recrystalized from ethanol, to give 5.58 g of 5-fluoro-3-methylthio-2-oxindole, m.p. 151°–152° C.

Analysis: Calcd. for $C_9H_8ONFS$: C, 54.80; H, 4.09; N, 7.10%. Found: C, 54.74; H, 4.11; N, 7.11%.

A sample of the above 5-fluoro-3-methylthio-2-oxindole (986 mg, 5.0 mmol) was added to 2 teaspoonsful of Raney nickel under 50 ml of absolute ethanol, and then the reaction mixture was heated under reflux for 2 hours. The catalyst was removed by decantation and was washed with absolute ethanol. The combined ethanol solutions were evaporated in vacuo and the residue was dissolved in dichloromethane. The dichloromethane solution was dried ($Na_2SO_4$) and evaporated in vacuo to give 475 mg of 5-fluoro-2-oxindole, m.p. 121°–134° C.

In analogous fashion, 4-trifluoromethylaniline was reacted with t-butyl hypochlorite, ethyl 2-(methylthio)acetate and triethylamine followed by reduction of the 3-thiomethyl-5-trifluoromethyl-2-oxindole thus obtained with Raney nickel, to give 5-trifluoromethyl-2-oxindole, m.p. 189.5°–190.5° C.

PREPARATION 6

6-Chloro-5-fluoro-2-oxindole

To 130 ml of toluene was added, with stirring, 24.0 g (0.0.165 mole) of 3-chloro-4-fluoroaniline and 13.5 ml (0.166 mole) of pyridine. The resulting solution was cooled to ca. 0° C. and 13.2 ml (0.166 mole) of 2-chloroacetyl chloride was added. The reaction mixture was stirred at room temperature for 5 hours and then it was extracted twice with 100 ml of 1N hydrochloric acid, followed by 100 ml of saturated sodium chloride solution. The resulting toluene solution was dried using magnesium sulfate, and then it was concentrated in vacuo to give 32.6 g (88% yield) of N-(2-chloroacetyl)-3-chloro-4-fluoroaniline.

A 26.63-g sample of the N-(2-chloroacetyl)-3-chloro-4-fluoroaniline was thoroughly mixed with 64 g of anhydrous aluminum chloride, and the mixture was heated at 210°–230° C. for 8.5 hours. The reaction mixture was then poured onto a mixture of ice and 1N hydrochloric acid, with stirring. Stirring was continued for 30 minutes, and then the solid was collected by filtration (22.0 g). The solid was dissolved in 1:1 ethyl acetate-hexane and chromatographed on 800 g of silica gel. Elution of the column, followed by evaporation of the fractions, produced 11.7 g of the N-(2-chloroacetyl)-3-chloro-4-fluoroaniline, followed by 3.0 g of 6-chloro-5-fluoro-2-oxindole. The latter material was recrystallized from toluene to give 1.70 g (7% yield) of the title compound, m.p. 196°–206° C. Analysis by NMR spectroscopy indicated that the product was contaminated by some 4-chloro-5-fluoro-2-oxindole.

PREPARATION 7

6-Fluoro-5-methyl-2-oxindole

An intimate mixture of 11.62 g (57.6 mmol) of N-(2-chloroacetyl)-3-fluoro-4-methylaniline and 30.6 g (229.5 mmol) of anhydrous aluminum chloride was heated to 210°–220° C. After 4 hours, the reaction mixture was cooled and then added to 100 ml of 1N hydrochloric acid and 50 ml of ice. A tan solid formed, which was collected by filtration and recrystallized from aqueous ethanol. Three crops were obtained, weighing 4.49 g, 2.28 g and 1.0 g, respectively. The crop weighing 1.0 g was further recrystallized from water to give 280 mg of the title compound, m.p. 168.5°–171° C.

PREPARATION 8

6-Bromo-2-oxindole

To 9.4 g of sodium hydride was added 195 ml of dimethyl sulfoxide, followed by the dropwise addition of 22.37 ml of dimethyl malonate. At the end of the addition, the mixture was heated at 100° C. and maintained at that temperature for 40 minutes. At this point, 25 g of 1,4-dibromo-2-nitrobenzene was added all at once. The reaction mixture was maintained at 100° C. for 4 hours and then it was added to 1.0 liter of saturated ammonium chloride solution. The resulting mixture was extracted with ethyl acetate and the extracts were washed with ammonium chloride solution, water and saturated sodium chloride. The dried ($MgSO_4$) solvent was evaporated, and the residue was recrystallized from ethyl acetate-hexane to give 22.45 g of dimethyl 2-(4-bromo-2-nitrophenyl)malonate.

A solution of 17.4 g of dimethyl 2-(4-bromo-2-nitrophenyl)malonate and 4.6 g of lithium chloride in 150 ml of dimethyl sulfoxide was placed in an oil bath at 100° C. After 3 hours, the reaction mixture was cooled to room temperature and then it was poured into a mixture of 500 ml of ethyl acetate and 500 ml of saturated sodium chloride solution. The layers were separated and the aqueous layer was extracted with further ethyl acetate. The combined organic layers were washed with saturated sodium chloride solution, dried using sodium sulfate, and thene vaporated in vacuo. The residue was chromatographed using silica gel as adsorbant and ethyl acetate-hexane mixture as eluant. This afforded 9.4 g of methyl 2-(4-bromo-2-nitrophenyl)acetate.

To a solution of 7.4 g of methyl 2-(4-bromo-2-nitrophenyl)acetate in 75 ml of acetic acid was added 6.1 g of iron powder. The reaction mixture was placed in an oil bath at 100° C. After 1 hour, the solvent was removed by evaporation in vacuo, and the residue was dissolved in 250 ml of ethyl acetate. The solution was filtered, washed with saturated sodium chloride solution, dried using sodium sulfate, decolorized using activated carbon, and evaporated in vacuo. This afforded 5.3 g of 6-bromo-2-oxindole as a white crystalline solid, m.p. 213°–214° C.

In like manner, starting with 1,4,5-trichloro-2-nitrobenzene, 5,6-dichloro-2-oxindole was prepared, m.p. 209°–210° C.

PREPARATION 9

5-Bromo-2-oxindole can be prepared by bromination of 2-oxindole; see further Beckett et al., *Tetrahedron*, 24, 6093 (1963) and Sumpter et al., *Journal of the American Chemical Society*, 67, 1656 (1945).

5-n-Butyl-2-oxindole can be prepared by reaction of 5-n-butylisatin with hydrazine hydrate followed by sodium methoxide in ethanol, according to the procedure of Preparation 1. 5-n-Butylisatin can be prepared from 4-n-butylaniline by treatment with chloral hydrate and hydroxylamine, followed by cyclization with sulfuric acid, according to the procedure of Parts A and B of Preparation 3.

6-Fluoro-2-oxindole can be prepared according to Protiva et al., *Collection of Czechoslovakian Chemical Communications*, 44, 2108 (1979) and U.S. Pat. No. 4,160,032.

6-Trifluoromethyl-2-oxindole can be prepared according to Simet, *Journal of Organic Chemistry*, 28, 3580 (1963).

PREPARATION 10

5-Chloro-1-acetyl-2-oxindole

A mixture of 7.0 g (42 mmole) of 5-chloro-2-oxindole and 5.9 ml (63 mmole) of acetic anhydride was heated under nitrogen at reflux for 3.5 hours. The cooled reaction mixture was diluted with 300 ml of ethyl acetate, and the resulting solution was washed with aqueous sodium bicarbonate followed by saturated, aqueous sodium chloride solution. The ethyl acetate solution was then dried ($Na_2SO_4$) and evaporated in vacuo to give 8.3 g of a purple solid. The latter solid was purified by chromatography on silica gel, eluting with 2.5% ethyl acetate in dichloromethane, to give 6.0 g of crude title compound as a yellow solid. The latter solid was recrystallized from ca. 50 ml of ethanol to give 4.7 g of the title compound as pale yellow needles, m.p. 129°–130° C.

PREPARATION 11

Reaction of the appropriate 2-oxindole with the requisite acid anhydride, substantially according to the procedure of Preparation 10, afforded the following compounds:

1-acetyl-2-oxindole, m.p. 127°–129° C.;
5-chloro-1-isobutyryl-2-oxindole, m.p. 91°–93° C.; and
6-chloro-5-floro-1-acetyl-2-oxindole, m.p. 146°–148° C.

PREPARATION 12

By reaction of the appropriate 2-oxindole with the necessary acid anhydride, using the procedure of Preparation 10, the compounds in Table III can be prepared.

TABLE III

| X | Y | $R^2$ |
|---|---|---|
| 5-$CF_3$ | H | methyl |
| 5-F | H | ethyl |
| 6-Cl | H | ethyl |
| 7-F | H | methyl |
| 6-$CF_3$ | H | methyl |
| 4-Cl | H | methyl |
| 6-Br | H | methyl |
| 5-Cl | 6-Cl | n-hexyl |
| 5-F | 6-F | methyl |
| 5-$CH_3$ | H | ethyl |

TABLE III-continued

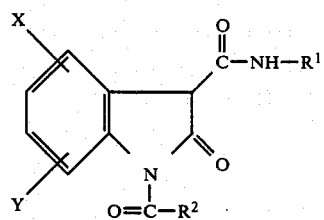

| X | Y | $R^2$ |
|---|---|---|
| 5-n-$C_4H_9$ | H | methyl |
| 4-$CH_3$ | 5-$CH_3$ | methyl |
| 5-$CH_3$ | 6-$CH_3$ | ethyl |
| 5-$CH_3$ | 6-F | methyl |
| H | H | isopropyl |

I claim:

1. A 1-acyl-2-oxindole-3-carboxamide compound of the formula and the pharmaceutically-acceptable base salts thereof; wherein X and Y are each selected from the group consisting of hydrogen, fluoro, chloro, bormo, trifluoromethyl and alkyl having 1 to 4 carbons;

$R^1$ is selected from the group consisting of heterocyclic, mono-methyl heterocyclic, furymethyl and thienylmethyl; wherein said heterocyclic is selected form the group consisting of pyridyl, thienyl, furyl, pyrrolyl, thiazolyl, oxazolyl, imidazolyl, isothiazolyl and isoxazolyl;

and $R^2$ is alkyl having 1 to 6 carbons.

2. A compound according to claim 1, wherein $R^1$ is furylmethyl or thienylmethyl.

3. A compound according to claim 2, wherein $R^2$ is methyl.

4. A compound according to claim 1, wherein $R^1$ is said heterocyclic or said mono-methyl heterocyclic.

5. The compound according to claim 3, wherein X and Y are each hydrogen and $R^1$ is 2-thienylmethyl.

6. The compound according to claim 4, wherein X is 5-chloro, Y is hydrogen and $R^1$ is 2-pyridyl.

7. A pharmaceutical composition, which comprises a pharmaceutically-acceptable carrier and a 1-acyl-2-oxindole-3-carboxamide compound according to claim 1, and wherein the weight ratio of the pharmaceutically-acceptable carrier to the 1-acyl-2-oxindole-3-carboxamide compound is in the range from 1:4 to 4:1.

8. A method of eliciting an analgesic response in a mammalian subject, which comprises administering to said mammalian subject an analgesic response eliciting amount of a 1-acyl-2-oxindole-3-carboxamide compound according to claim 1.

9. A method of treating an inflammatory disease in a mammalian subject, which comprises administering to said mammalian subject an inflammatory disease treating amount of a 1-acyl-2-oxindole-3-carboxamide compound according to claim 1.

* * * * *